United States Patent [19]

Vidéki et al.

[11] Patent Number: 5,043,153

[45] Date of Patent: Aug. 27, 1991

[54] COMPOSITIONS FOR THE PREVENTION AND MEDICAL TREATMENT OF PARODONTHOPATHY

[75] Inventors: Mihály Vidéki, Szabadszállás; József Váradi, Budapest; Katalin Mozsgai, Budapest; Zsuzsanna Kiss nee Váradi, Budapest; Géza Malasics, Budapest; Istvan Puskás, Budapest; Miklós Sipos, Budapest; Ottó Budavári, Budapest, all of Hungary

[73] Assignee: Fövárosi Tanács Gyógyszertári Központja, Budapest, Hungary

[21] Appl. No.: 339,003

[22] Filed: Apr. 17, 1989

[51] Int. Cl.$^5$ .................. A61K 7/16; A61K 35/78
[52] U.S. Cl. .................. 424/49; 424/195.1
[58] Field of Search .................. 424/49, 195.1

[56] References Cited

U.S. PATENT DOCUMENTS 4,104,373 8/1978 Sichert .................. 424/195.1
4,406,882 9/1983 Turner et al. .................. 424/49
4,683,133 7/1987 Southard .................. 424/49

Primary Examiner—Thurman K. Page
Assistant Examiner—G. S. Kishore
Attorney, Agent, or Firm—Schweitzer Cornman & Gross

[57] ABSTRACT

The invention relates to a composition for the prevention and medical treatment of parondonthopathy. The composition contains the aqueous or aqueous with other solvent extract of greater celandine (*Chelidonii herba*), peppermint leaf(*Menthae pip. fol.*), marigold (*Celendulae flos*), thyme (*Thymi herba*), millfoil (*Millefolii herba*), optionally chamomile (*Chamomillae flos*), melilot leaf (*Melissae fol.*), and clove (*Cariophylli flos*) or arnica (*Arnicae flos*).

5 Claims, No Drawings

COMPOSITIONS FOR THE PREVENTION AND MEDICAL TREATMENT OF PARODONTHOPATHY

FIELD OF THE INVENTION

The invention relates to a dentrifice composition containing a plurality of active ingredients, being suitable for the medical treatment or prevention of parodonthopathy.

BACKGROUND OF THE INVENTION

Various compositions are known for treating or preventing paradentosis or inflammation of the periodontium. It is a known important effort to prepare oral hygienic compositions contributing to prevention of different diseases of gum and to medical treatment of already developed illnesses.

Greater part of the pathological processes in the mouth are caused by fur (plaque) where the saliva as well as the microbiological and biochemical processes taking place on the surface of teeth and gum play an intermediate role.

DISCLOSURE OF THE INVENTION

It is an objective of the present invention to provide a composition from natural materials, which can widely be used against fungi, bacteria and viruses occurring in the mouth, and is suitable for inhibiting fur-formation, it has an activity of contraction and epithelization and it has an antiphlogistic, coagulant and no toxic effect.

The composition of the invention to be used for treatment and prevention of paradentosis and inflammation of the periodontium, preferably in the form of a dentrifice, such as a toothpaste or a mouthwash contains the extract of the active ingredients of the following plants: greater celandine (*Chelidonii herba*), milfoil (*Millefolii herba*), peppermint leaf (*Menthae pip. fol.*), thyme (*Thymi herba*), and marigold (*Calendulae flos*). The active ingredients of chamomile (*Chamomillae flos*), melilot leaf (*Melissae fol.*), clove (*Cariophylli flos*) or arnica (*Arnicae flos*) can also be added to the composition. The extract suitably contains 14-16.5 parts of greater celandine, 204 parts of peppermint leaf, 3-4 parts of thyme, 1-2 parts of marigold, 1.5-2.5 parts of milfoil, and if desired, 0.4-0.6 part of clove or 0.8 to 1.2 part of arnica.

The composition of the present invention can be prepared as follows: an extract is prepared from the mixture of fresh or dried, perhaps crushed effective parts of the plants, i.e. from 14-16.5 parts of greater celandine (*Chalidonium herba*), 2-4 parts of peppermint leaf (*Menthae pipl. fol.*), 3-4 parts of thyme (*Thymi herba*), 1-2 parts of marigold (*Calendulae flos*) with 5-10-fold amount of water calculated on the plant part, with ethanol or the mixtures thereof, then it is converted, if desired, into a dentrifice such as a mouthwash or toothpaste by adding other additives that are known per se. Before preparing the extract it can be preferable to swell the plant parts in an extracting agent. Triethanolamine or glycerine can be used as an additive.

A most suitable extracting agent is the mixture of ethanol and water, and perhaps flavored with xylith when used as a mouthwash. When preparing toothpaste sodium fluoride, gel forming agents, other flavoring agents, volatile oil components, tanning agents, and fluoro salts can be added to the plant-extract.

The extract of plants is prepared by extracting by any known method, such as soaking, percolation, extraction in counterflow or extraction under overpressure with carbon dioxide or nitrogen gas.

The following can be used as active ingredient or additives in preparing the compositions:

biological active ingredients as flavonoides, active alkaloids, fluoro salts, gel forming agents, as acrylic acid derivatives, methylcellulose derivatives, detergents such as sodium lauryl sulfate, (e.g. Medialen LD from Hoechst AG.), preservatives: sorbic acid, nypagine, glycerine, triethanolamine, abrasives: aluminum salts, calcium carbonate, dicalcium phosphate, flavoring agents: volatile oils, anise, mentha, clove, cinnamon, phenylsalicylate, sweeteners: xylith and sorbite.

The composition of the present invention for preventing and treatment is suggested to be administered twice of three times a day in form of e.g. medicated toothpaste or mouthwash or given as 1 teaspoon thereof in 0.5 dl. of water.

The antibiotic and antiinflammatory effect of greater celandine is increased by the other active ingredient components. The volatile oil-content is important concerning the microbiological activity of terpene and phenyl propane derivatives being present, first of all the disinfecting activity of thymol and its similar derivatives should be mentioned. Menthol is important because of its seasoning, cooling and mild anaesthetic effect, owing to their contracting, hemostatic and epithelium-forming effect the flavonoides and tanning agents present strengthen the gum, decrease the inflammation and atrophic processes and disinfect the mouth cavity.

The characteristic contents and active ingredients, especially the alcaloids, volatile oils, flavonoides and tanning agents being of special importance concerning the oral hygienic usability can be shown in the compositions according to the invention on the basis of phytochemical analysis.

In addition to the antibacterial, fungicidal and antiviral activity and antiinflammatory features the compositions according to the invention have also contractive, hemostatic and epithelization-promoting effect, which effects are summarized in the inhibition of fur-formation. The near neutral pH-value of the composition does not sour the natural pH-value of the mouth.

The preparation of the compositions according to the invention is described in detail in the following Examples:

EXAMPLE 1

30 g. of dried and crushed plant part mixture is prepared containing the following components:

16.5 parts of greater celandine
2 parts of milfoil
2 parts of chamomile
2 parts of peppermint leaf
3 parts of thyme
3 parts of marigold
1 part of melilot leaf
0.5 part of clove
1 part of arnica.

The plant mixture is soaked for 10 days in a 45% water-ethanol mixture, then swollen and 300 g. of a solvent mixture is used under continuous stirring.

After extraction the plant parts are pressed and extraction is completed to 300 g. with the solvent mixture, then precipitates and filtered.

A medicated mouthwash is obtained which is favored with xylith for children.

Dry-substance content is about 1.74 g./100 ml., the extract has mildly bitterish after-taste.

EXAMPLE 2

The extract according to Example 1 is used for preparing a toothpaste and it is concentrated with fluoro salt.

12 g. of carboxymethyl starch are swollen using the mixture of sodium fluoride dissolved in 40 g. of distilled water and 2.0 g. of glycerine, then 40 g of the plant extract of Example 1 are added. Previously 0.1 g. of sorbic acid and 1.2 g. of triethanolamine, then 3 g. of sodium-lauryl-sulfate are mixed to the gel. Chlorophyll is dissolved in the flavoring and medicating volatile oil components (20 drops of clove, anise and cinnamon oil and phenyl salicylate) and mixed to the gel.

The biological activity of the prepared compositions was examined on a group of patients, first of all the immunity from fur of the teeth (purity of mouth) and bleeding index. The modified Cohen-index shows the formation of fur on the teeth by numbers between 0 and 5, with the value being 0 when there is no fur, and ⅔ of the crown of the tooth is covered by fur at the value of 5.

The bleeding index was also measured by the numbers between 0 and 5, where at 0 no inflammation occurred and bleeding did not occur even for a mild pressure of probe, while at 5 bleeding showed up without any stimulation, a change of color and conspicuous tumefaction could be observed with ulceration.

On the basis of the Mühlemann-index from 100 of patients 21 completely recovered while the status of 78 improved, resulting in an average improvements of 0.77.

On the basis of the Cohen-index the fur decreased to 0 in the case of 4 patients and improved in 95 patients. The average improvement was 0.83.

Decrease of the index values and the improvement in the status of patient show that the examined compositions have fur-decreasing and anti-gingivital effect.

The composition is therefore effective in the primary prevention and treatment of paradentosis and in inflammation of the periodontium.

It has neither deleterious side-effect nor any effect that would cause an allergic reaction.

The fur-decreasing effect of the composition is near 1 as measured by the Cohen-index, i.e. the composition is able to remove the fur from ⅓ of the tooth surface. As a natural consequence the gum-bleeding index (Mühlemann) decreases. Therefore the composition is suitable for prevention and medical treatment of gingivitis, paradentosis and inflammation of the periodontium, by which higher treatment costs can be saved in addition to prevention in the field of prosthetic dentistry. (Mühlemann-type Sulcus Bleeding Index-Renggli H. H.: Auswirkungen subgingival approximaler Füllungsränder auf den Entzündungsgrad der benachbarten Gingiva, Eine klinische Studie, Schweiz, Mschr. Zahnheikunde 84, 181, 1974).

We claim:

1. A dental treatment composition comprising as an active ingredient an extract or mixture of extracts with water or with water and another solvent of the herbs from 14–16.5 parts greater celandine (*Chelidonii herba*), from 2–4 parts of peppermint leaf (*Monthae pip. fol.*), from 1 to 2 parts of marigold (*Calendulae flos.*), from 1.5 to 2.5 parts of thyme (*Thymia herba*), and from 1.5 to 2.5 parts milfoil (*Millefolii herba*).

2. The dental treatment composition of claim 1, further comprising an additional extract or mixture of extracts of one or more of chamomile (*Chamomillae flos*), melilot leaf (*Melissa fol.*), and clove (*Cariophylli flos*) or arnica (*Arnieae flos*).

3. The dental treatment composition of claim 2, wherein the amount of each of any one or more of said additional extracts present is 2 parts of chamomile, 1 part of melilot leaf, and 0.4 to 0.6 parts of clove or of arnica.

4. The dental treatment composition of claim 1, wherein the entirety of the extracts comprises from 5 to 10 times the solids content of the extracts.

5. The dental treatment composition of claim 1, wherein the extract comprises an aqueous alcoholic solvent containing from 40 to 50 mass % ethanol.

* * * * *